United States Patent
Burke et al.

(10) Patent No.: US 6,679,226 B2
(45) Date of Patent: Jan. 20, 2004

(54) FUEL SENSOR SYSTEM

(75) Inventors: David H. Burke, Flint, MI (US); Michael J. Niemiec, Brighton, MI (US); Charles R. Harrington, Troy, MI (US); David K. Lambert, Sterling Heights, MI (US); Han-Sheng Lee, Bloomfield Hills, MI (US); Su-Chee S. Wang, Troy, MI (US)

(73) Assignee: Delphi Technologies, Inc., Troy, MI (US)

( * ) Notice: Subject to any disclaimer, the term of this patent is extended or adjusted under 35 U.S.C. 154(b) by 91 days.

(21) Appl. No.: 09/997,371

(22) Filed: Nov. 30, 2001

(65) Prior Publication Data

US 2003/0101972 A1 Jun. 5, 2003

(51) Int. Cl.$^7$ .............................................. F02M 37/04
(52) U.S. Cl. ...................................... 123/509; 123/514
(58) Field of Search ................................ 123/509, 514, 123/510; 417/87

(56) References Cited

U.S. PATENT DOCUMENTS

| | | | | |
|---|---|---|---|---|
| 3,497,134 A | * | 2/1970 | Horn ............................ | 417/48 |
| 5,218,942 A | * | 6/1993 | Coha et al. .................. | 123/514 |
| 5,237,975 A | | 8/1993 | Betki et al. | |
| 5,327,872 A | * | 7/1994 | Morikawa ..................... | 123/516 |
| 5,379,741 A | | 1/1995 | Matysiewicz et al. | |
| 5,448,977 A | | 9/1995 | Smith et al. | |
| 5,636,616 A | * | 6/1997 | Okane et al. ................. | 123/514 |
| 5,791,317 A | * | 8/1998 | Eck .............................. | 123/510 |
| 5,848,583 A | | 12/1998 | Smith et al. | |
| 5,960,775 A | * | 10/1999 | Tuckey ......................... | 123/509 |
| 6,123,511 A | * | 9/2000 | Sertier ........................... | 417/87 |

* cited by examiner

Primary Examiner—Mahmoud Gimie
(74) Attorney, Agent, or Firm—Jimmy L. Funke

(57) ABSTRACT

A fuel sensor system for a vehicle includes a fuel pump adapted to be disposed in a fuel tank to pump fuel from the fuel tank to an engine of the vehicle. The fuel sensor system also includes a fuel sensor adapted to be disposed in the fuel tank to measure a property index of the fuel. The fuel sensor system further includes a jet pump connected to the fuel pump to fill the fuel sensor with a fuel sample of the fuel.

21 Claims, 2 Drawing Sheets

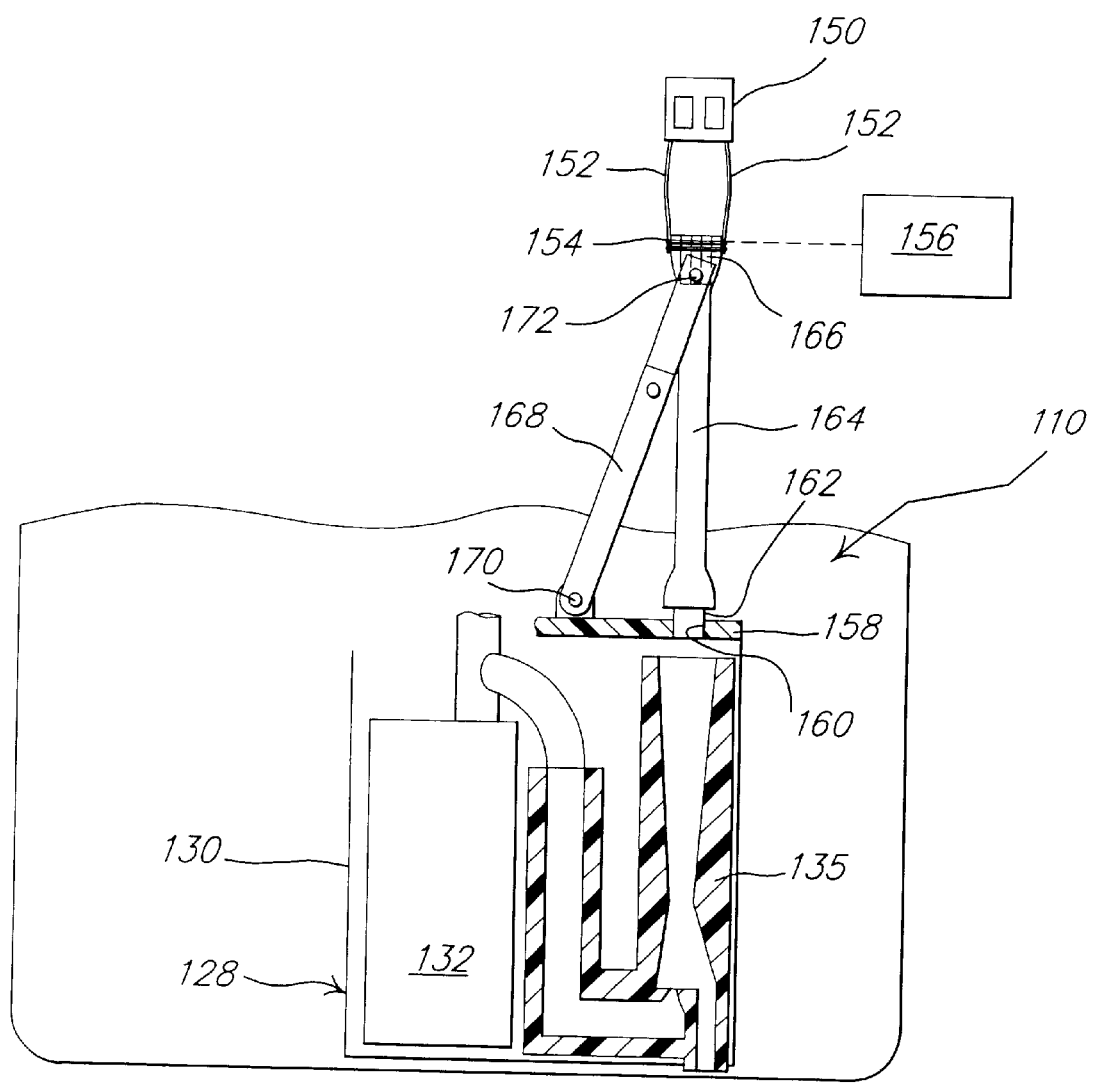

FUEL SENSOR SYSTEM

TECHNICAL FIELD

The present invention relates generally to fuel systems for vehicles and, more particularly, to a fuel sensor system for a fuel system of a vehicle.

BACKGROUND OF THE INVENTION

It is known to provide a fuel system for a vehicle, which includes a fuel tank, a fuel delivery module, a fuel filter, a fuel pressure regulator, a fuel rail, and fuel injectors. In the fuel system, a fuel pump of the fuel delivery module typically runs at a maximum flow at all times to deliver fuel to an engine of the vehicle. When the engine is turned off, heat from the engine continues to heat the fuel rail and causes the pressure in the fuel rail to rise. The increased pressure causes the fuel pressure regulator to open and relieve the pressure by dumping the heated fuel into the fuel tank, which generates vapor in the fuel tank.

As emission regulations for vehicles become tighter, new ways to decrease emissions are desired. For exhaust hydrocarbon (HC) emissions, the air-to-fuel ratio during cold start is a critical variable. If the air-fuel mixture is too rich, extra exhaust HC is emitted. If the air-fuel mixture is too lean, the engine has poor performance. It is known that gasoline type fuel varies in volatility. One approach to improve control of the air-to-fuel ratio during cold start is to measure the drivability index (DI) of the fuel at the end of each trip, just after the engine is turned off. The measured value is stored and used in a fueling algorithm for the cold start at the beginning of the next trip.

To measure the DI, a small sample of fuel is heated in the fuel tank, and its evaporation is monitored as a function of temperature or time. An interdigitated sensor can be used to monitor the evaporation. An example of such interdigitated sensor is described in pending U.S. patent application Ser. No. 09/924,873 filed Aug. 8, 2001.However, the interdigitated sensor needs to be contacted by the fuel before the measurement can be made.

It is desirable to contact a fuel volatility sensor with fuel before a measurement of drivability index of the fuel is made. It is also desirable to provide fuel to a fuel volatility sensor in a fuel system of a vehicle. It is further desirable to obtain a fuel sample for a fuel volatility sensor in a fuel system of a vehicle. Therefore, there is a need in the art to provide a fuel sensor system for a fuel system that meets these desires.

SUMMARY OF THE INVENTION

It is, therefore, one object of the present invention to provide a fuel sensor system for a fuel system of a vehicle.

It is another object of the present invention to provide a system that obtains a fuel sample for a fuel volatility sensor to measure a property of the fuel such as a drivability index of the fuel.

To achieve the foregoing objects, the present invention is a fuel sensor system for a vehicle including a fuel pump adapted to be disposed in a fuel tank to pump fuel from the fuel tank to an engine of the vehicle. The fuel sensor system also includes a fuel sensor adapted to be disposed in the fuel tank to sense a property of the fuel. The fuel sensor system further includes a jet pump connected to the fuel pump to fill the fuel sensor with a fuel sample of the fuel.

One advantage of the present invention is that a fuel sensor system is provided for a vehicle. Another advantage of the present invention is that the fuel sensor system uses a jet pump to deluge a fuel volatility sensor to measure a property of the fuel such as the drivability index of the fuel. Yet another advantage of the present invention is that the fuel sensor system obtains a fuel sample for a fuel volatility sensor without adding any moving parts. Still another advantage of the present invention is that the fuel sensor system samples fuel for a fuel volatility sensor that is relatively less expensive and bulky without moving parts.

Other objects, features, and advantages of the present invention will be readily appreciated, as the same becomes better understood, after reading the subsequent description taken in conjunction with the accompanying drawings.

BRIEF DESCRIPTION OF THE DRAWINGS

FIG. 3 is a fragmentary elevational view of another embodiment, according to the present invention, of the fuel sensor system of FIG. 1.

DESCRIPTION OF THE PREFERRED EMBODIMENT

Figure 1:
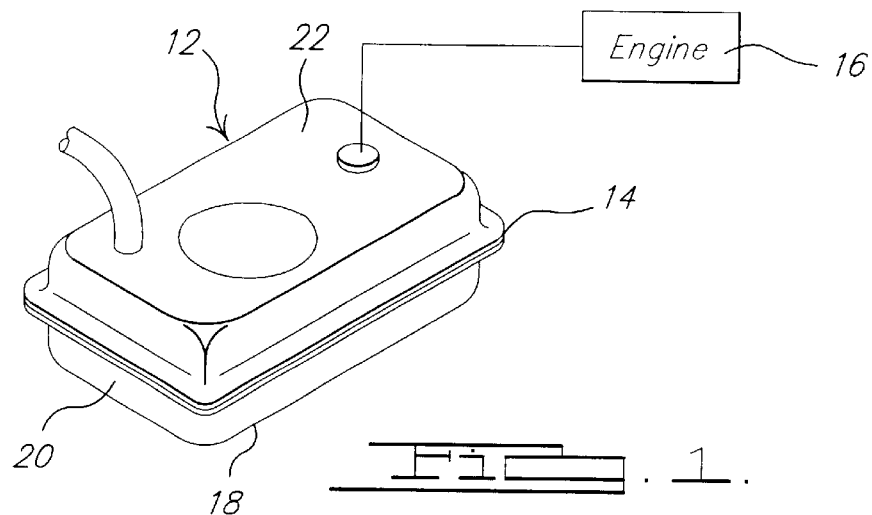
FIG. 1 is a diagrammatic perspective view of a fuel sensor system, according to the present invention, illustrated in operational relationship with a fuel system and engine of a vehicle.
Figure 2:
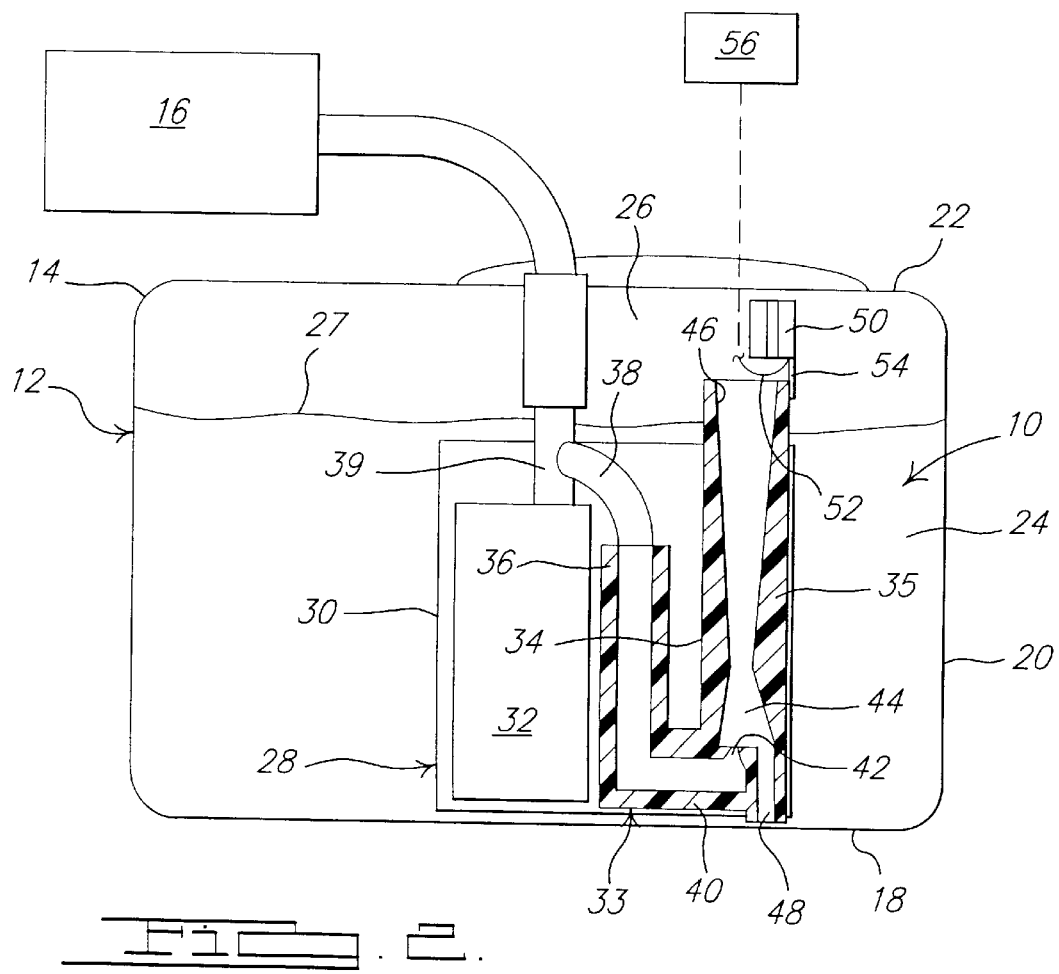
FIG. 2 is a fragmentary elevational view of the fuel sensor system, fuel system, and engine of FIG. 1.

Referring to the drawings and in particular FIGS. 1 and 2, one embodiment of a fuel sensor system 10, according to the present invention, is shown for a fuel system, generally indicated at 12, of a vehicle (not shown). The fuel system 12 supplies fuel from a fuel tank 14 to an engine 16 of the vehicle. The fuel tank 14 is used to hold liquid fuel. In this embodiment, the fuel tank 14 includes a bottom or base wall 18 and a side wall 20 around a periphery of the base wall 18 and extending generally perpendicular thereto. The fuel tank 14 also includes a top wall 22 extending generally perpendicular to the side wall 20 to form an interior chamber 24. The fuel tank 14 also includes a vapor space 26 formed above a liquid fuel 27 in the fuel tank 14. The fuel tank 14 is made of a rigid material, preferably a plastic material. It should be appreciated that the fuel tank 14 could be made of a metal material such as steel. It should also be appreciated that the fuel tank 14 is conventional and known in the art.

The fuel sensor system 10 also includes a fuel delivery module, generally indicated at 28, disposed in the fuel tank 14 to deliver fuel from the fuel tank 14. The fuel delivery module 28 includes a fuel reservoir 30 disposed in the interior chamber 24 of the fuel tank 14 and a fuel pump 32 disposed in the fuel reservoir 30 to pump fuel therefrom to the engine 16. The fuel pump 32 is electrically driven and connected to a source of power (not shown). The fuel pump 32 is sized by the cold start requirements of the fuel system 12. It should be appreciated that the fuel pump 32 is disposed in the fuel reservoir 30 and the fuel reservoir 30 maintains fuel at the fuel pump 32 under low fuel conditions. It should also be appreciated that the fuel reservoir 30 and fuel pump 32 are conventional and known in the art.

The fuel sensor system 10 also includes a jet pump, generally indicated at 33, disposed in the fuel reservoir 30 of the fuel tank 14, and fluidly connected to the fuel pump 32. The jet pump 33 includes a venturi pump 34 and a standpipe 35 connected to the venturi pump 34. The venturi pump 34 is generally "L" shaped and has an upper end 36 fluidly connected by a conduit 38 to an outlet 39 of the fuel pump 32. The venturi pump 34 has a lower end 40 with an orifice 42 to pass fuel therethrough. The standpipe 35 extends vertically from the lower end 40 of the venturi pump 34 and has a chamber 44 at a lower end thereof adjacent the orifice 42. The standpipe 35 has an outlet 46 at an upper end thereof communicating with the chamber 44. The standpipe 35 also has an inlet 48 at a lower end thereof communicating with the chamber 44. The fuel reservoir 30 is kept full by the venturi pump 34, which passes a small amount of the high pressure fuel from the fuel pump 32 through the orifice 42 through which it expands into the chamber 44, causing a pressure drop which draws in fuel from the inlet 48. The jet pump 33 is made of a rigid material such as plastic. The jet pump 33 is a monolithic structure being integral, unitary, and one-piece.

The fuel sensor system 10 further includes a sensor 50 disposed, preferably, in the vapor space 26 in the interior chamber 24 of the fuel tank 14. The sensor 50 may be of an interdigitated type. The sensor 50 is mounted above the outlet 46 of the standpipe 35 such that fuel exiting the standpipe 35 flows onto the sensor 50. The sensor 50 is positioned so that it is in a flow of liquid fuel while the fuel pump 32 is On. It should be appreciated that the sensor 50 senses a property of the fuel such as the volatility of the fuel. It should also be appreciated that the sensor 50 may sense other properties than fuel volatility such as alcohol content.

The sensor 50 may be mounted to the standpipe 35. In one embodiment, to allow the excess liquid fuel to drain away, the sensor 50 is mounted by connecting wires 52, with the connecting wires 52 below the sensor 50, so that excess liquid can drain down the connecting wires 52 from the lowest point of the sensor 50. In one embodiment, the connecting wires 52 are attached to the standpipe 35 by at least one, preferably a pair of plastic cable ties 54. In this embodiment, the sensor 50 is mounted at least seven millimeters (7 mm) above the fuel level in the fuel tank 14. It should be appreciated that the sensor 50 needs to be mounted so that excess liquid on the outside can drain off it, otherwise, the fuel remaining on the outside constitutes an uncontrolled volume. It should also be appreciated that the sensor 50 needs to be mounted above the fuel level, otherwise, fuel continuously replaces fuel being evaporated, producing a source of error. It should further be appreciated that the sensor 50 may be of the type described in pending U.S. patent application Ser. No. 09/924,873 filed Aug. 8, 2001, the disclosure of which is hereby incorporated by reference.

The fuel sensor system 10 also includes an electronic controller 56 electrically connected to the sensor 50. The controller 56 receives and stores the value of the fuel property such as drivability index measured by the sensor 50 for use in a fuel algorithm to adjust an air-to-fuel ratio to the engine 16. It should be appreciated that the controller 56 may be a separate controller or some other controller in the vehicle.

In operation, liquid fuel in the interior chamber 24 of the fuel tank 14 is pumped by the fuel pump 32 through the fuel line into the engine 16. The sensor 50 is located in the vapor space 26 of the fuel tank 14, above the maximum fill level. The sensor 50 is positioned so that it is in a flow of liquid fuel while the fuel pump 32 is On. When the fuel pump 32 is On, the sensor 50 is in contact with fuel. A test is performed when the engine 16 is turned off, thus shutting off the fuel pump 32. The sensor 50 retains a fuel sample after the fuel pump 32 has been turned Off by capillary action between plates (not shown) of the sensor 50. Excess liquid drains down the wires 52 that are used for a support. In one embodiment, the sensor 50 is heated by the controller 56 a predetermined time interval after the fuel pump 32 has been turned Off to sense the volatility of the fuel. After the fuel pump 32 is turned Off, a predetermined time interval such as five seconds is sufficient before the beginning of the measurement. Capacitance of the sensor 50 is measured as a function of temperature of the sensor 50 as the fuel is heated. The presence of ethanol in the fuel and the fuel volatility are determined by the controller 56 from the measurements. It should be appreciated that the output of the jet pump 33 is used to deluge the sensor 50, mounted above the outlet of the standpipe 35 such that fuel exiting the standpipe 35 flows onto the sensor 50.

In another embodiment, the speed of the fuel pump 32 is controlled to bring fuel to the sensor 50 when desired. In this way, a measurement of fuel volatility can be performed while the engine 16 is On, but with the speed of the fuel pump 32 reduced such that the fuel level is below the sensor 50.

In yet another embodiment, the sensor 50 is placed inside a fixture (not shown) mounted on top of the low-pressure flow tube. Fuel fills the fixture when the fuel pump 32 is On and the sensor 50 is submerged. After the fuel pump 32 is turned Off, the liquid returns to its static level and the sensor 50 retains a fuel sample. It should be appreciated that any type of sensor may be used to determine properties of fuel or other liquids in automotive and non-automotive applications.

Referring to FIG. 3, still another embodiment, according to the present invention, of the fuel sensor system 10 is shown. Like parts of the fuel sensor system 10 have like reference numerals increased by one hundred (100). In this embodiment, the fuel sensor system 110 includes the fuel delivery module 128 having a deflector 158 mounted to the fuel reservoir 130 and located above the standpipe 135. The deflector 158 is a plate having an aperture 160 extending therethrough. The deflector 158 is made of a rigid material such as plastic. It should be appreciated that the deflector 158 deflects some of the fuel from the standpipe 135 into the fuel reservoir 130.

The fuel sensor system 110 also includes a fitting 162 disposed in the aperture 160 of the deflector 158 and extending upwardly. The fitting 162 has a smaller diameter passageway (not shown) extending axially therethrough to act as a jet. The fitting 162 is made of a rigid material such as brass. The fuel sensor system 110 includes a tube or conduit 164 having a lower end attached to the fitting 162 and extending upwardly. The conduit 164 is made of a plastic material such as nylon. The fuel sensor system 110 also includes a fitting 166 attached to the upper end of the conduit 164. The fitting 166 has a smaller diameter passageway (not shown) extending axially therethrough to act as a jet. The fitting 166 is made of a rigid material such as brass. The fuel sensor system 110 includes the sensor 150 mounted by the connecting wires 152 to the fitting 166 in a manner to be described, with the connecting wires 52 below the sensor 150, so that excess liquid can drain down the connecting wires 152 from the lowest point of the sensor 150. The fuel sensor system 110 includes a mechanical fixture 168 that clamps over the fitting 166 at the end of the conduit 164 and holds the fitting 166 securely. The connecting wires 152 are attached to the fixture 168 and conduit 164 by at least one, preferably a pair of plastic cable ties 154. The fuel sensor system 110 further includes a threaded rod 170 to mechanically connect or support the fixture 168 to the fuel reservoir 134. It should be appreciated that the fixture 168 may have a screw 172 to apply the clamping force to the fitting 166.

In operation, when the fuel pump 132 is On, most of the fuel flowing up the standpipe 135 is deflected by the deflector 160 into the fuel reservoir 130. A portion of the fuel from the standpipe 135 flows up the conduit 164 and is ejected out the end of the fitting 166 as a jet. The jet of fuel impinges on the sensor 150 while the fuel pump 132 is On. The test is typically performed when the engine 16 is turned off, thus turning off the fuel pump 132. The sensor 150 retains a fuel sample after the fuel pump 132 has been turned Off by capillary action between plates (not shown) of the sensor 150. The remaining operation of the fuel sensor system 110 is similar to the fuel sensor system 10.

The present invention has been described in an illustrative manner. It is to be understood that the terminology, which has been used, is intended to be in the nature of words of description rather than of limitation.

Many modifications and variations of the present invention are possible in light of the above teachings. Therefore, within the scope of the appended claims, the present invention may be practiced other than as specifically described.

What is claimed is:

1. A fuel sensor system for a vehicle comprising:
    a fuel pump adapted to be disposed in a fuel tank to pump fuel from the fuel tank to an engine of the vehicle;
    a fuel sensor adapted to be disposed in the fuel tank and located in a vapor space of the fuel tank to sense a property of the fuel; and
    a jet pump connected to said fuel pump and having an outlet positioned beneath said fuel sensor such that fuel exiting said jet pump flows onto said fuel sensor to fill said fuel sensor with a fuel sample of the fuel.

2. A fuel sensor system as set forth in claim 1 including a fuel reservoir adapted to be disposed in the fuel tank, said fuel pump and said jet pump being disposed in said fuel reservoir.

3. A fuel sensor system as set forth in claim 1 wherein said jet pump has an inlet.

4. A fuel sensor system as set forth in claim 1 wherein said jet pump comprises a venturi pump having a first outlet fluidly connected to said fuel pump and a first inlet.

5. A fuel sensor system as set forth in claim 4 wherein said jet pump further comprises a standpipe connected to said venturi pump.

6. A fuel sensor system as set forth in claim 5 wherein said standpipe has an interior chamber, said first inlet of said venturi pump being disposed in said chamber, a second inlet at a lower end communicating with said chamber, and a second outlet at an upper end communicating with said chamber.

7. A fuel sensor system as set forth in claim 5 including a deflector mounted to said fuel reservoir above said standpipe to deflect some of the fuel from said standpipe into said fuel reservoir.

8. A fuel sensor system as set forth in claim 4 wherein said sensor has wires extending downwardly from said sensor.

9. A fuel sensor system as set forth in claim 6 including a connector to connect said sensor to said second outlet of said standpipe.

10. A fuel sensor system as set forth in claim 1 including an electronic controller electrically connected to said sensor to receive a signal from said sensor.

11. A fuel system for a vehicle comprising:
    a fuel tank having an interior chamber;
    a fuel pump disposed in said interior chamber of said fuel tank to pump fuel therefrom;
    a fuel volatility sensor disposed in said fuel tank and located in a vapor space of the fuel tank to sense volatility of the fuel; and
    a jet pump disposed in said fuel tank and having an outlet positioned beneath said fuel volatility sensor such that fuel exiting said jet pump flows onto said fuel volatility sensor, said jet pump being connected to said fuel pump to fill said fuel volatility sensor with a fuel sample of the fuel.

12. A fuel system as set forth in claim 11 including a fuel reservoir disposed in said fuel tank, said fuel pump and said jet pump being disposed in said fuel reservoir.

13. A fuel system as set forth in claim 11 wherein said jet pump has an inlet.

14. A fuel system as set forth in claim 11 wherein said jet pump comprises a venturi pump having a first outlet fluidly connected to said fuel pump and a first inlet.

15. A fuel system as set forth in claim 11 wherein said jet pump further comprises a standpipe connected to said venturi pump.

16. A fuel system as set forth in claim 15 wherein said stand pipe has an interior chamber, said first inlet of said venturi pump being disposed in said chamber, a second inlet at a lower end communicating with said chamber, and a second outlet at an upper end communicating with said chamber.

17. A fuel system as set forth in claim 16 wherein said sensor has wires extending downwardly from said sensor.

18. A fuel system as set forth in claim 17 including a connector to connect said sensor to said second outlet of said standpipe.

19. A fuel system as set forth in claim 11 including an electronic controller electrically connected to said sensor to heat said sensor.

20. A method of operating a fuel sensor system for a vehicle, said method comprising the steps of:
    disposing a fuel pump and a jet pump in a fuel tank and fluidly connecting the jet pump to the fuel pump;
    disposing a sensor in the fuel tank located in a vapor space of the fuel tank and above an outlet of the jet pump;
    pumping fuel from the fuel tank to an engine of the vehicle with a fuel pump;
    pumping fuel onto the sensor by the jet pump and retaining a sample of the fuel by the sensor.

21. A method as set forth in claim 20 including the step of sensing a property of the fuel with the fuel sensor.

* * * * *